United States Patent [19]

Klopfer et al.

[11] Patent Number: 4,460,798

[45] Date of Patent: Jul. 17, 1984

[54] PROCESS FOR PREPARATION OF ASYMMETRICAL BISPHENOLS

[75] Inventors: Howard J. Klopfer, Clifton Park; Charles M. Orlando, Scotia, both of N.Y.

[73] Assignee: General Electric Company, Schenectady, N.Y.

[21] Appl. No.: 471,598

[22] Filed: Mar. 3, 1983

[51] Int. Cl.$^3$ .............................................. C07C 39/16
[52] U.S. Cl. ..................................... 568/723; 568/722
[58] Field of Search ................................ 568/722, 723

[56] References Cited

U.S. PATENT DOCUMENTS 2,597,717  5/1952  Faith ................................... 568/722
4,239,918  12/1980 Keeley ................................ 568/722

FOREIGN PATENT DOCUMENTS 693145  8/1964  Canada ................................. 568/722
2035323 6/1980  United Kingdom ................. 568/722

OTHER PUBLICATIONS

Kammer et al., "Chemical Abstracts", vol. 55, 14369–14377, (1961).

*Primary Examiner*—Werren B. Lone
*Attorney, Agent, or Firm*—William H. Pittman; James C. Davis, Jr.; James Magee, Jr.

[57] ABSTRACT

Asymmetrical bisphenols such as 2-(3-hydroxyphenyl)-2-(4-hydroxyphenyl)propane are prepared by an improved process wherein a hydroxyphenyldialkylcarbinol is reacted with a phenol in the presence of a hydrogen halide catalyst. According to the improved process, the carbinol is added to a mixture of the phenol and hydrogen halide under conditions maintaining a low carbinol concentration in the reaction mixture. This low concentration is preferably maintained by adding the carbinol in the form of a solution in a portion of the phenol.

8 Claims, No Drawings

PROCESS FOR PREPARATION OF ASYMMETRICAL BISPHENOLS

This invention relates to the preparation of asymmetrical bisphenols by alkylation of phenols. In its broadest sense the invention is directed to an improvement in a process for the preparation of asymmetrical bisphenols by the alkylation of at least one phenol with at least one hydroxyaryldialkylcarbinol in the presence of a hydrogen halide, said improvement comprising adding said hydroxyaryldialkylcarbinol to a liquid mixture of said phenol and said hydrogen halide under conditions maintaining a low concentration of said hydroxyaryldialkylcarbinol in the reaction mixture.

Asymmetrical bisphenols are known to be useful as intermediates for the formation of various polymers such as polycarbonates; reference is made to U.S. Pat. No. 4,237,259. According to U.S. Pat. No. 4,239,918, such bisphenols may be prepared by alkylating phenol with a hydroxyphenyl-$\alpha,\alpha$-dialkylbenzyl alcohol (also known as a hydroxyaryldialkylcarbinol and sometimes referred to hereinafter simply as a "carbinol") in the presence of an acidic catalyst. Typical acidic catalysts disclosed therein are sulfuric acid and hydrogen chloride, the latter of which may be used in gaseous form or in aqueous solution as hydrochloric acid.

Several problems have arisen in the preparation of asymmetrical bisphenols by the above-described method. For the most part, these problems are a result of the tendency of carbinols to undergo self-condensation. For example, 3-hydroxyphenyldimethylcarbinol readily condenses with itself to form 1,3-bis-(3-hydroxyphenyl)-1,1-dimethyl-2-butene. Under most conditions, the self-condensation reaction is favored over phenol alkylation.

The sulfuric acid-catalyzed alkylation reaction has been found disadvantageous on a large scale in that it is too slow to compete effectively with self-condensation. A similar problem is encountered when a mixture of the phenol and the carbinol is saturated with hydrogen chloride; self-condensation of the carbinol then occurs so rapidly that the yield of asymmetrical bisphenol is substantially lowred. Self-condensation can be suppressed to some extent by maintaining a very high molar ratio of phenol to carbinol, typically at least 6:1 and preferably as high as 8:1. However, it then becomes necessary to remove the excess phenol by distillation, which consumes a large amount of energy. Moreover, self-condensation is still a serious problem when such a process is effected on a large scale.

A principal object of the present invention, therefore, is to provide an improved process for the preparation of asymmetrical bisphenols by alkylation of phenols under acidic conditions.

A further object is to provide a process by which asymmetrical bisphenols can be prepared in relatively high yield on a large scale with minimum by-product formation.

A still further object is to prepare such bisphenols by a process offering maximum convenience and efficiency with minimum energy usage.

Other objects will in part be obvious and will in part appear hereinafter.

Suitable phenols for use in the process of this invention include phenol itself (i.e., hydroxybenzene) and substituted phenols such as the cresols and alkoxyphenols having at least one unsubstituted ortho- or para-position, preferably para.

The alkyl groups in the hydroxyaryldialkylcarbinol usually contain from one to about four carbon atoms and are preferably primary alkyl groups; examples are methyl, ethyl, propyl, n-butyl and isobutyl. They are most often methyl. The hydroxyaryl group is preferably otherwise unsubstituted, but may contain substituents such as hydroxy, nitro, methoxy, halo, carboxy or the like. Examples of suitable hydroxyaryl groups are 2-hydroxyphenyl, 3-hydroxyphenyl, 3-hydroxy-4-nitrophenyl, 2-methoxy-3-hydroxyphenyl, 1-hydroxy-2-naphthyl and 4-hydroxy-1-naphthyl. Hydroxyphenyl groups, especially 3-hydroxyphenyl, are most preferred. Thus the carbinol most often used is 3-hydroxyphenyldimethylcarbinol. Mixtures of carbinols may also be used.

The hydrogen halide used as an alkylation catalyst in the process of this invention may be hydrogen fluoride, hydrogen chloride, hydrogen bromide or hydrogen iodide. Hydrogen chloride is preferred for reasons of availability and economy.

According to this invention, the carbinol is added to a liquid mixture of the phenol and the halogen acid under conditions maintaining a low concentration of said carbinol in the reaction mixture. Typically, the concentration of unreacted carbinol at any time is kept below about 20% by weight, preferably about 5–15%. This low concentration may be maintained in a number of ways. For example, addition of the carbinol may be very slow, so that it does not substantially exceed the rate of the alkylation reaction. Alternatively, the carbinol may be diluted with a substantially inert diluent such as an aliphatic or aromatic hydrocarbon, provided the amount of diluent is not so great as to retard the alkylation reaction so that it does not compete effectively with self-condensation.

The preferred method of maintaining low carbinol concentration is to add the carbinol in the form of a mixture with a portion of the phenol, normally in liquid form as a solution therein. In general, the carbinol concentration in such a mixture should not exceed about 35% by weight. There is no mandatory lower limit of carbinol concentration, but there is little or no advantage in employing mixtures containing less than about 25% carbinol.

According to the process of this invention in its preferred embodiment, gaseous hydrogen chloride is bubbled through a portion of the phenol at a temperature of about 40°–60° C. and a solution of carbinol in the balance of the phenol is added slowly thereto. The total mole ratio of phenol to carbinol is typically from about 4:1 to about 8.5:1, with a sufficient portion of phenol being used as a solvent for carbinol to provide about a 25–35% solution of the latter. Addition is normally effected slowly and the reaction mixture is agitated during the addition. The reaction is complete soon after all of the solution of carbinol in phenol has been added. The product is typically isolated by removing excess phenol by distillation, usually under vacuum, followed by recrystallization from a suitable solvent.

When compared with other typical methods for the preparation of asymmetrical bisphenols, the process of this invention affords the product in a shorter time and better yield when operated on a large scale. It also minimizes the formation of undesirable by-products. Moreover, the use of hydrogen fluoride or chloride simplifies product recovery since acid can be easily removed by distillation or evaporation; the use of sulfuric acid necessitates removal by more costly water extraction. In addition, this method is capable of being operated with lower ratios of phenol to carbinol, minimizing the need for distillation and recycle of phenol and therefore permitting a decrease in energy consumption.

The following examples illustrate the advantages provided by the invention. Examples 1 and 4 are illustrations of the process of this invention, and Examples 2 and 3 of other processes for carrying out the same reaction.

EXAMPLE 1

Phenol, 3750 grams (39.7 moles), was heated to 42° C. with stirring and was saturated with gaseous hydrogen chloride. Additional hydrogen chloride was bubbled through the mixture as a solution of 1500 grams (9.8 moles) of 3-hydroxyphenyldimethylcarbinol in 3750 grams (39.7 moles) of phenol was added over 3 hours. After addition was complete, the mixture was vacuum distilled; the hydrogen chloride and excess phenol were removed at 60° C./0.2 torr. Distillation was complete when the pot temperature was 120° C. The distillation residue was cooled to 100° C. and dissolved in 5 liters of toluene. Upon cooling the toluene solution, the desired 2-(3-hydroxyphenyl)-2-(4-hydroxyphenyl)propane was precipitated; it was isolated by filtration, washed with cold toluene and dried under vacuum. The yield was 1914 grams (85% of theoretical). The product was identified by melting point (97°–98° C.), vapor phase chromatography and proton nuclear magnetic resonance, all of which showed it to be identical with authentic samples.

EXAMPLE 2

Gaseous hydrogen chloride was bubbled for 10 seconds through a solution of 30 grams (0.197 mole) of 3-hydroxyphenyldimethylcarbinol in 150 grams (1.59 moles) of phenol at 50° C., with stirring. An exothermic reaction took place and the reaction mixture was cooled to maintain the temperature below 63° C., as hydrogen chloride passage was continued for 15 minutes. Upon distillation of the excess phenol as in Example 1, and recrystallization of the distillation residue from chloroform followed by filtration and drying, there was obtained 10.9 grams (24% of theoretical) of the desired 2-(3-hydroxyphenyl)-2-(4-hydroxyphenyl)propane.

EXAMPLE 3

A mixture of 1335 grams (14.2 moles) of phenol, 450 ml. of 75% aqueous sulfuric acid and 1800 ml. of toluene was stirred at room temperature while a solution of 450 grams (2.9 moles) of 3-hydroxyphenyldimethylcarbinol in 890 grams (9.5 moles) of phenol and 1800 ml. of toluene was added over three hours. The reaction mixture was stirred at room temperature for four hours and the aqueous layer was separated and discarded. The organic layer was washed twice with water, once with 10% sodium bicarbonate solution and again with water. Toluene and excess phenol were removed by vacuum distillation and the residue was recrystallized from toluene. There was obtained 371 grams (55% of theoretical) of the desired 2-(3-hydroxyphenyl)-2-(4-hydroxyphenyl)propane.

EXAMPLE 4

The procedure of Example 1 is repeated, except that a total of 3685 grams (39.2 moles) of phenol is used, with 1842.5 grams being used as a solvent for the carbinol. Similar results are obtained.

As will be apparent from the above examples, the process of this invention yields asymmetrical bisphenol in unexpectedly high yield at relatively short reaction times, with a minimum of processing steps and by-product formation.

What is claimed is:

1. In a process for the preparation of asymmetrical bisphenols by the alkylation of at least one phenolic compound selected from the group consisting of phenol and substituted phenols having at least one unsubstituted ortho- or para-position with at least one hydroxyaryldialkylcarbinol in which the alkyl groups contain from one to about four carbon atoms in the presence of a hydrogen halide at a temperature of about 40°–60° C., the improvement which comprises adding said hydroxyaryldialkylcarbinol to a liquid mixture of said phenolic compound and said hydrogen halide under conditions such that the concentration of said hydroxyaryldialkylcarbinol in the reaction mixture is kept below about 20% by weight.

2. A process according to claim 1 wherein the hydrogen halide is hydrogen chloride.

3. A process according to claim 2 wherein the low concentration of said hydroxyaryldialkylcarbinol is maintained by adding the same in liquid form as a solution in a portion of the phenol.

4. A process according to claim 3 wherein the alkyl groups in the hydroxyaryldialkylcarbinol are methyl groups.

5. A process according to claim 4 wherein the concentration of hydroxyaryldialkylcarbinol in the solution thereof in the phenol is about 25–35% by weight.

6. A process according to claim 5 wherein the total mole ratio of phenol to hydroxyaryldialkylcarbinol is from about 4:1 to about 8.5:1.

7. A process according to claim 1 wherein the phenolic compound is phenol; that is, hydroxybenzene.

8. A process according to claim 7 wherein the hydroxyaryldialkylcarbinol is 3-hydroxyphenyldimethylcarbinol.

* * * * *